United States Patent [19]

Juneja

[11] 4,067,962

[45] Jan. 10, 1978

[54] ORAL COMPOSITIONS CONTAINING TRIFLUOROMETHYL PHENYL BIS-BIGUANIDES AS ANTIPLAQUE AGENTS

[75] Inventor: Prem Sagar Juneja, Cincinnati, Ohio

[73] Assignee: The Procter & Gamble Company, Cincinnati, Ohio

[21] Appl. No.: 669,930

[22] Filed: Mar. 24, 1976

Related U.S. Application Data

[63] Continuation-in-part of Ser. No. 601,244, Aug. 1, 1975, abandoned.

[51] Int. Cl.$^2$ .......................... A61K 7/18; A61K 7/22; C07C 129/16
[52] U.S. Cl. .................................. 424/52; 260/501.14; 260/564 B; 260/565; 424/48; 424/49; 424/54; 424/316; 424/326
[58] Field of Search ............... 260/565, 564 B, 501.14; 424/48, 49, 54, 52, 316

[56] References Cited

U.S. PATENT DOCUMENTS 4,001,393  1/1977  L'Orange ............................... 424/52

OTHER PUBLICATIONS

Warner et al., J. Med. Chem., vol. 16, pp. 732–733, (1973).

Primary Examiner—Gerald A. Schwartz
Attorney, Agent, or Firm—Ronald L. Hemingway; George W. Allen; Richard C. Witte

[57] ABSTRACT

Oral compositions such as toothpastes, mouthwashes, and the like containing certain trifluoromethylphenyl bis-biguanides having excellent antiplaque performance and reduced tendency to stain the teeth.

20 Claims, No Drawings

ORAL COMPOSITIONS CONTAINING TRIFLUOROMETHYL PHENYL BIS-BIGUANIDES AS ANTIPLAQUE AGENTS

CROSS REFERENCE TO RELATED APPLICATION

This application is a continuation-in-part of the abandoned application of Prem S. Juneja having Ser. No. 601,244, filed Aug. 1, 1975.

BACKGROUND OF THE INVENTION

The field of this invention is "oral compositions" which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes and topical solutions.

The bis-biguanide antibacterial agents such as chlorhexidine, 1,6 bis($N^5$-p-chlorophenyl-$N^1$-biguanido) hexane, are known to be effective antiplaque agents, but it has been recognized that they have a tendency to produce severe staining of the teeth. Belgian Pat. No. 801,703, issued Jan. 4, 1973, discloses the use of the insoluble salts of the bis-biguanides in oral compositions as a means of reducing the stain problem. Belgian Pat. No. 811,878, issued Sept. 4, 1974, U.S. patent application Ser. No. 495,951, filed Aug. 9, 1974, (and its continuation-in-part Ser. No. 584,304, filed June 6, 1975) and U.S. patent application Ser. No. 563,988, filed Apr. 1, 1975, (and its continuation-in-part Ser. No. 652,092, filed Jan. 27, 1976) disclose the use of metal ion chelator compounds, such as amino acids, aminopolycarboxylates and hydroxypyrones, with the bis-biguanides to reduce stain. My concurrently-filed copending application having Ser. No. 670,518 (continuation-in-part of Ser. No. 589,232, filed June 23, 1975) discloses certain bisbiguanides, wherein the bridging alkylene group has from 1 to 4 carbon atoms instead of six, which have substantially lower staining tendencies then chlorhexidine.

DESCRIPTION OF THE INVENTION

It has now been discovered that certain novel bis-biguanide compounds wherein the bridging alkylene group is $C_1$ to $C_4$ alkylene, and wherein the terminal nitrogen atoms contain trifluormethylphenyl groups, have outstanding antiplaque activity and very low tendency to stain the teeth.

The novel bis-biguanide compounds of this invention have the generic formula

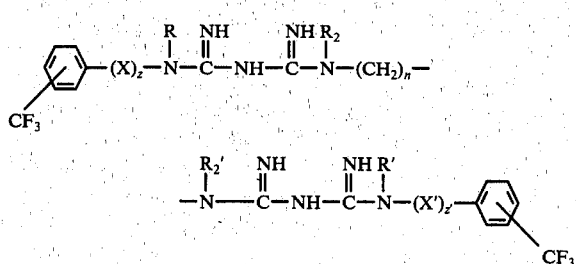

wherein $n$ is from 1 to 4 inclusive (preferably 2 to 4 inclusive); wherein X and X' each represent an alkylene radical containing from 1 to 3 carbon atoms; wherein $z$ and $z'$ each can be either 0 or 1; wherein R and R', each represent either hydrogen, an alkyl radical containing from 1 to about 12 carbon atoms, or an aralkyl radical containing from 7 to about 12 carbon atoms and wherein $R_2$ and $R_2'$ each represent either hydrogen or an alkyl radical of 1 to 2 carbon atoms. Preferred is the compound wherein $z$ and $z'$ are each 0, $n$ is 2 and R, R', $R_2$ and $R_2'$ are hydrogen. Preferably, the trifluoromethyl group is in the meta position; however, the corresponding ortho and para isomers are also suitable for use herein. The pharmaceutically acceptable salts of the foregoing compounds are especially desirable. The water soluble salts, especially the dihydrochloride, digluconate and diacetate salts, are the most desirable since they make possible the formation of clear solution compositions. In contrast with chlorhexidine, whose dihydrochloride salt is insoluble in water, the hydrochlorides of the compounds of the present invention are water-soluble. Typically, the hydrochloride salt is inherently formed in the preparation of chlorhexidine and of the compounds of the present invention. For purposes of this application, water-soluble salts are considered to be those having a solubility of greater than about 0.04% by weight in water at 25° C.

Examples of bis-biguanides falling within the scope of the present invention are the following:

Bis($N^5$-m-trifluoromethylphenyl-$N^1$-biguanido)methane 1,2-bis($N^5$-m-trifluoromethylphenyl-$N^1$-biguanido)ethane, 1,4-bis($N^5$-m-trifluoromethylphenyl-$N^1$-biguanido)butane, 1,2-bis($N^5$-m-trifluoromethylbenzyl-$N^1$-biguanido)ethane, 1,2-bis($N^5$-p-trifluoromethylphenyl-$N^1$-biguanido)ethane, 1,2-bis($N^5$-o-trifluoromethylphenyl-$N^1$-biguanido)ethane, 1,2-bis($N^5$-m-trifluoromethylphenyl-$N^5$-hexyl-$N^1$-biguanido)ethane, 1,2-bis($N^5$-m-trifluoromethylphenyl-$N^5$-2-phenethyl-$N^1$-biguanido)ethane, 1,2-bis($N^5$-m-trifluoromethylphenyl-$N^1$-ethyl-$N^1$-biguanido)ethane, 1,4-bis($N^5$-m-trifluoromethylphenyl-$N^5$-ethyl-$N^1$-methyl-$N^1$-biguanido)butane, 1,2-bis($N^5$-m-trifluormethyl-$N^5$-methyl-$N^1$-ethyl-$N^1$-biguanido)-ethane, and their water soluble salts, for example, the digluconate, dihydrochloride and diacetate salts. The most preferred compounds are 1,2-bis($N^5$-m-trifluoromethylphenyl-$N^1$-biguanido)-ethane and its dihydrochloride, diacetate and digluconate salts.

The compounds of the invention can be made by reacting ethylene or methylene diamine dihydrochloride (or an appropriately N,N' substituted ethylene or methylene diamine dihydrochloride) with sodium dicyanamide to give, for example, a bis($N^3$-cyano-$N^1$-guanidino)ethane, which is then reacted with the hydrochloride of the desired m-trifluoromethyl phenylamine to give the desired bis-biguanide compound in the form of its hydrochloride salt. The general preparation procedure for bis-biguanides is well known in the art; see, for example, Warner et al. J. Pharm. Sci. 62 No. 7, 1189–91 (1973) and Rose et al. J. Chem. Soc. 4422 (1956).

The novel bis-biguanide antiplaque agents of the present invention are utilized in oral hygiene in the form of oral compositions which comprise from about 0.01% to about 2.5% (preferably from about 0.05% to about 1.2%, and most preferably from about 0.1% to about 0.8%) by weight of the bis-biguanide antiplaque agent and the balance, a carrier suitable for use in the oral cavity. All percentages herein are by weight, unless specified otherwise. Depending upon the composition, lesser or greater amounts may be used. In general, all that is required is to have an effective amount of the bis-biguanide compound in the mouth sufficient to give antiplaque and/or anticaries effectiveness. Generally, an amount of 0.001 grams or more per usage of the bis-biguanide can be considered as an effective amount for plaque control.

The pH of the compositions of this invention is preferably maintained within the range of from about 4.5 to about 9.5. Below about 4.5, damage to dental enamel can occur. Above about 9.5, the alkalinity becomes cosmetically undesirable and may irritate soft tissue in the mouth.

As previously stated, compositions of the present invention comprise the aforedescribed bis-biguanide antiplaque agents and a carrier suitable for use in the oral cavity. The carrier can be water or an organic solvent such as alcohol. Preferably, however, the carrier portion of the oral composition is a conventional toothpaste, mouthwash, chewing gum or the like.

Dentifrices contain an abrasive polishing material and typically also contain sudsing agents, flavoring and sweetening agents. Toothpastes usually additionally contain humectants and binders and water. The dentifrices herein comprise from about 0.5% to about 95% abrasive in addition to the bis-biguanide antiplaque agent.

Any abrasive polishing material which does not excessively abrade dentin can be used in these dentifrice compositions. These include, for example, calcium carbonate dicalcium orthophosphate dihydrate, calcium pyrophosphate, calcium polymetaphosphate and insoluble sodium polymetaphosphate. Preferably, however, the abrasive is one which has a high degree of compatibility with the bis-biguanide. These include, for example, condensation products of urea and formaldehyde such as disclosed by Cooley et al. in U.S. Pat. No. 3,070,510, granted Dec. 25, 1962, silica xerogels such as those disclosed in U.S. Pat. No. 3,538,230 to Pader et al., issued Nov. 3, 1970, hydrofluoric acid-treated amorphous silica abrasives such as those disclosed in U.S. Pat. No. 3,862,307 to DiGiulio, issued Jan. 21, 1975, and mineral abrasives coated with cationic polymers such as those disclosed in U.S. Ser. No. 471,941, Benedict, filed May 21, 1974. The abrasives generally have a particle size of from about 0.1 to about 20 microns in diameter.

The total amount of abrasive materials in the dentifrice embodiments of this invention can range from 0.5% to 95% by weight of the dentifrice. Preferably, toothpastes contain from about 6% to about 60%, and toothpowders contain from about 20% to about 95% abrasives.

Dentifrices usually contain surface-active agents (also called sudsing agents).

Suitable surface-active agents are those which are reasonably stable and form suds throughout a wide pH range, and which will not react with the bis-biguanide compound, i.e., nonsoap nonionic, cationic, zwitterionic and amphoteric organic synthetic detergents.

The nonionic synthetic detergents which can be used with the oral compositions of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula,

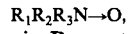

wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula $$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide, 2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide 3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water solubilizing group, e.g., carboxy, sulfonate, sulfate, phosphate, or phosphonate. A general formula for these compounds is:

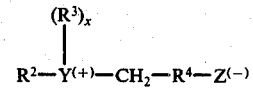

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; $x$ is 1 when Y is a sulfur atom and 2 when Y is a nitrogen or phosphorus atoms, $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradecoxylphosphonio]-2-hydroxypropane-1-phosphate;
3[N,N-dipropyl-N-3-dodecoxy-2-hydroxypropylammonio]-propane1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]2-hydroxypentane-1-sulfate.

The cationic synthetic detergents useful in the oral compositions of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethyldimethylbenzylammonium chloride; coconutalkyltrimethylammonium nitrite; cetyl pyridinium fluoride; etc. Especially preferred are the quaternary ammonium fluorides described in Briner et al, U.S. Pat. No. 3,535,421, issued Oct. 20, 1970, incorporated by reference, where said quaternary ammonium fluorides have detergent properties.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxylate, sulfonate, sulfate, phosphate, or phosphonate. Examples of compounds falling within this definition are sodium 3-dodecylaminopropionate, sodium 3-dodecylaminopropane sulfonate, dodecyl-beta-alanine, N-alkyl-taurines such as the one prepared by reacting dodecylamine with sodium isethionate according to the teaching of Kosmin, U.S. Pat. No. 2,658,072, issued Nov. 3, 1973, N-higher alkyl aspartic acids such as those produced according to the teaching of Lynch, U.S. Pat. No. 2,438,091, issued Nov. 16, 1948, and the products sold under the trade name "Miranol" and described in Mannheimer, U.S. Pat. No. 2,528,378 issued Oct. 31, 1950.

Many additional nonionic, cationic, zwitterionic and amphoteric synthetic detergents are known to the art and can be used as sudsing agents in the compositions herein. Further examples can be found in *McCutcheon's Detergents and Emulsifiers*, 1972 Annual, published by Allure Publishing Corporation, which is incorporated herein by reference.

The sudsing agent can be employed at levels ranging from about 0.5% to about 5.0% of the dentifrice composition.

Dentifrices normally also contain flavoring agents. Suitable flavoring agents for use in the dentifrices herein include, for example, wintergreen oil (methyl salicylate), oil of peppermint, oil of sassafras (synthetic), and oil of anise. Flavoring agents are present at a level of from 0.01% to 2.0%.

Dentifrices normally also contain sweetening agents. Suitable sweetening agents for use in dentifrices include, for example, saccharin, dextrose and levulose. The sweetening agents are used at levels of from about 0.05% to about 2%.

In toothpastes it is desirable to employ thickening agents such as hydroxyethylcellulose and water-soluble salts of cellulose ethers, including sodium carboxymethyl cellulose and sodium carboxymethylhydroxyethyl cellulose; or natural gums, including gum karaya, gum arabic and gum tragacanth. Also, colloidal magnesium aluminum silicate or finely divided silica can be used as part of the thickening agent to improve the texture of the product. Thickening agents are used at levels of from 0.1% to 5.0% of the toothpaste composition.

It is also desirable to include a humectant material in toothpastes. Suitable materials for this purpose include glycerine, sorbitol, and other edible polyhydric alcohols or mixtures thereof. These materials can comprise from about 1% to about 50% of the toothpaste composition. In addition to the aforementioned typical components of a toothpaste, water usually comprises the balance of the toothpaste, and is usually present at levels up to about 50%.

Mouthwashes generally comprise a water/ethyl alcohol solution and optionally other ingredients such as flavor, sweeteners, and humectants such as those mentioned above for dentifrices. The alcohol provides an antibacterial effect. Optionally, mouthwashes also contain sudsing agents such as those mentioned above for dentifrices. Humectants such as glycerine and sorbitol give a moist feel in the mouth and are desirably also present. Antibacterial agents are sometimes incorporated into mouthwashes (or dentifrices) at levels from about 0.01% to about 2.0%.

Generally, mouthwashes suitable for use as carriers herein contain 5% to 40% ethyl alcohol, 0% to 20% (preferably 5% to 20%) glycerine or other humectant, 0% to 2% (preferably 0.1% to 2%) sudsing agent, 0% to 0.5% (preferably 0.05% to 0.5% sweetening agent such as saccharin and 0% to 0.3% (preferably 0.05% to 0.3%) flavoring agent, and the balance, water.

Chewing gum suitable for use as a carrier herein comprises a gum base and flavoring materials such as those mentioned above for dentrifrices. The flavoring materials are present at a level of 0.01% to about 2.0% of the final chewing gum composition. The gum base is a chewable plastic gum material such as natural rubber, chicle, polyvinyl acetate, ester gum, coumarone resin, and paraffin wax. The gum base is typically made from a mixture of two or more plastic gum materials to achieve a preferred degree of plasticity for chewing. Optionally, corn syrup is added as a softener and binder for the chewing gum and sugar is optionally added as a filler and sweetener. A typical chewing gum suitable as a carrier herein comprises 15% to 30% gum base, 15% to 20% corn syrup, 50% to 65% sugar, and 0.05% to 1.5% flavoring materials.

Lozenges suitable as carriers herein comprise a hard sugar candy base and one or more flavoring materials. The flavoring materials are present at levels between 0.1% and 2.0%. Optionally, lozenges can contain various other materials. A typical lozenge suitable as a carrier in this invention is a hard candy comprised of a hard candy base containing 0.05% to 1.5% flavor. The hard candy base is a solidified solution of amorphous sugar which is generally formed from a sugar solution which has been cooked at high temperature so as to remove nearly all of the moisture.

The flavoring materials and antiplaque agent are added before the moisture is removed. The flavoring materials mentioned hereinbefore for dentrifrices are also exemplary of those suitable for use in lozenges.

When formulating the antiplaque agents of the present invention into an oral composition, the amount which is incorporated into the composition should be sufficient to provide at least 0.001 grams of antiplaque agent per usage of the composition. Thus, in dentifrices, where the amount of product used per usage is from about 1 to 4 grams, the amount of antiplaque agent in the dentifrice should be at least about 0.03%, preferably from about 0.1% to about 2%, and most preferably from about 0.5% to about 1.5%. In mouthwashes, typical usage is from about 10 to 20 grams, and the amount of antiplaque agent in the mouthwash should be at least 0.01, preferably from about 0.5% to about 1.5%, and most preferably from about 0.1% to about 1.0%.

Typical usage of chewing gum and lozenges is from about 1 to 4 grams and the amount of antiplague agent in the chewing gum or lozenge should be at least about 0.03%, preferably from about 0.1% to about 2%, and most preferably from about 0.5% to about 1.5%.

Generally, oral compositions should contain from about 0.01% to about 2.5% of the antiplaque agent.

The oral compositions of the present invention can also optionally contain additional therapeutic materials for use in the oral cavity such as anticaries agents, (e.g., water-soluble fluoride such as sodium fluoride and stannous fluoride) and anticalculus agents such as trisodium ethane 1-hydroxy-1,1-diphosphonate.

Although the novel bis-biguanide compounds of the present invention give considerably less staining of the teeth than chlorhexidine, they are not completely free of staining potential and it is, therefore, often desirable to include in the compositions of the invention certain chelating agents which are useful in combating the general tendency of bis-biguanide antiplaque agents to stain the teeth, as well as the tendency of the teeth to become stained from natural causes such as contact with certain foods and beverages. Such chelating agents are disclosed in Haefele, U.S. Pat. No. 3,937,807, issued Feb. 10, 1996; U.S. Ser. No. 584,304, Gieske and Juneja, filed June 6, 1975; and U.S. Ser. No. 652,692, Gieske and Juneja, filed Jan. 27, 1976. Examples of chelating agents useful for this purpose are nitrilotriacetic acid, ethylenediamine diacetic acid, kojic acid, maltol, ethyl maltol, calcium dihydrogen ethylenediamine tetraacetate, di-N-substituted ethylene diamine diacetic acids wherein the substituents can be ethyl or 2-hydroxyethyl. The pharmaceutically acceptable water-soluble salts of these chelators are particularly useful, e.g., the sodium, potassium and ammonium salts. When a chelator is used, enough chelator should be present in the compositions such that some excess chelator is present in addition to that which reacts or would react with the bis-biguanide present. The concentration of such excess chelator generally ranges from about 0.01% to about 1.25% by weight of the composition. Generally, two moles of chelator react with one mole of bisbiguanide compound.

This invention will be further illustrated by the following examples:

EXAMPLE I

A toothpaste is prepared according to the following formula:

| Component | Parts by weight |
| --- | --- |
| Sorbitol (70% soln.) | 20.00 |
| Sodium saccharin | 0.21 |
| Veegum (colloidal magnesium aluminum silicate) | 0.40 |
| Precipitated urea/formaldehyde condensate (abrasive) | 30.00 |
| Flavor | 1.00 |
| Sodium carboxymethylcellulose | 1.30 |
| Glycerine | 10.00 |
| 1,2-bis(N$^5$-m-bifluoromethylphenyl-N'-biguanido)-ethane digluconate | 0.70 |
| Polyoxyethylene sorbitan (20) monoisostearate | 1.50 |
| Distilled water | balance to 100 |

This toothpaste, when used in the normal manner, is effective in retarding the formation of dental plaque and produces an appreciably lower level of stain on the teeth than does chlorhexidine.

EXAMPLE II

A mouthwash in accordance with the present invention is formulated as follows:

| Component | Parts by weight |
| --- | --- |
| Ethyl alcohol (95% in water) | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Flavoring | 0.16 |
| 1,2-bis(N$^5$-m-trifluoromethylphenyl-N'-biguanido)ethane dihydrochloride | 0.20 |
| Color | 0.50 |
| Sorbitol (70% in water) | 12.00 |
| Distilled water | balance to 100 |

When used in the normal manner to rinse the mouth, this product is effective in retarding the formation of dental plaque and produces an appreciably lower level of stain on the teeth than does chlorhexidine.

EXAMPLE III

A chewing gum in accordance with the present invention is formulated as follows:

| Component | Parts by weight |
| --- | --- |
| Gum Base | 21.30 |
| Ester Gum | 6.40 |
| Coumarone resin | 9.60 |
| Dry latex rubber | 3.20 |
| Paraffin wax (M.P.180° F.) | 2.10 |
| Sugar | 58.45 |
| Corn Syrup (Baume 45) | 18.20 |
| Flavoring | 1.05 |
| 1,2-bis(N$^5$-m-trifluoromethylphenyl-N'-biguanido)ethane diacetate | 1.00 |

Chewing this gum in the normal manner retards the formulation of dental plaque and produces appreciably less staining of the teeth than does chlorhexidine.

EXAMPLE IV

When in the preceding examples the 1,2-bis(N$^5$-m-trifluoromethylphenyl-N$^1$-biguanido)ethane salts are replaced by the digluconate or diacetate salts of the following compounds, similar results are obtained in that antiplaque performance is obtained with appreciably less staining to the teeth than is obtained if chlorhexidine is used:

1,4-bis(N$^5$-m-trifluoromethylphenyl-N$^1$-biguanido)butane, 1,2-bis(N$^5$-m-trifluoromethylbenzyl-N$^1$-biguanido)ethane, 1,2bis(N$^5$-m-trifluoromethylphenyl-N$^5$-hexyl-N-$^1$-biguanido)ethane, 1,2-bis(N$^5$-m-trifluoromethylphenyl-N$^5$-2-phenethyl-N$^1$-biguanido)ethane 1,4-bis(N$^5$-m-trifluoromethylphenyl-N$^5$-ethyl-N$^1$-methyl-N$^1$-biguanido)butane, 1,2-bis(N$^5$-m-trifluoromethylbenzyl-N$^5$-methyl-N$^1$-biguanido)ethane, 1,2-bis(N$^5$-m-trifluoromethylphenyl-N$^5$-phenethyl-N$^1$-biguanido)ethane, 1,2-bis(N$^5$-p-trifluoromethylphenyl-N$^1$-biguanido)ethane, 1,2-bis(N$^5$-o-trifluoromethylphenyl-N$^1$-biguanido)ethane, Bis-(N$^5$-m-trifluoromethylphenyl-N$^1$-biguanido)methane.

What is claimed is:

1. A bis-biguanide compound having the generic formula:

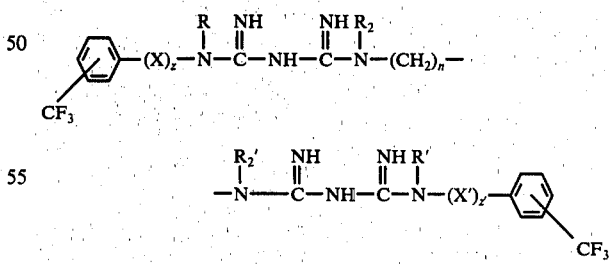

wherein $n$ is from 2 to 4 inclusive; wherein X and X' each represent an alkylene radical containing from 1 to 3 carbon atoms; wherein $z$ and $z'$ are selected from the group consisting of 0 to 1; wherein R and R' are each selected from the group consisting of hydrogen, alkyl radicals containing from 1 to about 12 carbon atoms and aralkyl radicals containing from 7 to about 12 carbon atoms; and wherein $R_2$ and $R_2'$ are each selected from the group consisting of hydrogen and alkyl radicals of 1 to 2 carbon atoms; and the pharmaceutically acceptable salts thereof.

2. The compound of claim 1 wherein said salt is a water-soluble salt.

3. The compound of claim 2 wherein the salt is selected from the group consisting of the dihydrochloride, diacetate and digluconate salts.

4. The compound of claim 1 wherein $n$ equals 2, $z$ and $z'$ are each O and R, R', $R_2$ and $R_2'$ are each hydrogen.

5. The compound of claim 4 wherein the trifluoromethyl groups are in the meta position.

6. The compound of claim 4 wherein said compound is a pharmaceutically acceptable, water-soluble salt.

7. The compound of claim 5 wherein said compound is a pharmaceutically acceptable, water-soluble salt.

8. The compound of claim 7 wherein said salt is selected from the group consisting of the dihydrochloride diacetate and digluconate salts.

9. An oral composition comprising a carrier suitable for use in the oral cavity and from about 0.01% to about 2.5% of an antiplaque agent having the formula:

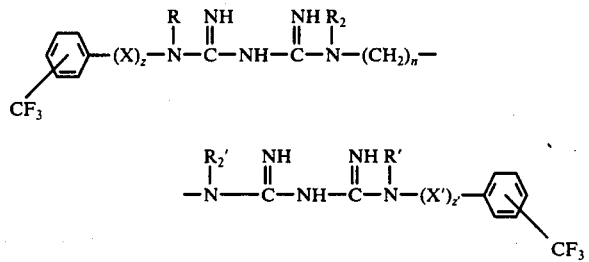

wherein $n$ is from 2 to 4 inclusive; wherein X and X' each represent an alkylene radical containing from 1 to 3 carbon atoms; wherein $z$ and $z'$ each are selected from the group consisting of 0 to 1; wherein R and R' are selected from the group consisting of hydrogen, alkyl radicals containing from 1 to about 12 carbon atoms and aralkyl radicals containing from 7 to about 12 carbon atoms and wherein $R_2$ and $R_2'$ each are selected from the group consisting of hydrogen and alkyl radicals of 1 to 2 carbon atoms, and the pharmaceutically acceptable salts thereof.

10. The composition of claim 9 wherein said antiplaque agent is in the form of a water-soluble, pharmaceutically acceptable salt.

11. The composition of claim 10, wherein said salt is selected from the group consisting of the dihydrochloride, diacetate and digluconate salts.

12. The composition of claim 9 wherein $n$ equals 2, $z$ and $z'$ are each O and R, R', $R_2$ and $R_2'$ are each hydrogen.

13. The composition of claim 12 wherein the trifluoromethyl groups in the antiplaque agent are in the meta position.

14. The composition of claim 12 wherein said antiplaque agent is a pharmaceutically acceptable water-soluble salt.

15. The composition of claim 13 wherein said antiplaque agent is in the form of a pharmaceutically acceptable water-soluble salt.

16. The composition of claim 15 wherein said salt is selected from the group consisting of the dihydrochloride, diacetate and digluconate salts.

17. The compositions of claim 16 wherein the amount of antiplaque agent in said composition is from about 0.05% to about 1.2%.

18. The composition of claim 16 in the form of a dentifrice wherein said antiplaque agent is present at a level of from about 0.1% to about 2.0% and wherein said composition contains as an additional ingredient from about 0.5% to about 95% of an abrasive.

19. The composition of claim 16 in the form of a mouthwash wherein said antiplaque agent is present at a level of from about 0.5% to about 1.5% and wherein said composition contains as additional components:
A. from about 5% to about 40% ethyl alcohol;
B. from 0% to about 20% humectant;
C. from 0% to about 2% sudsing agent;
D. from 0% to about 0.5% sweetening agent;
E. from about 0.05% to about 0.3% flavoring agent; and
F. the balance water.

20. A composition in accordance with claim 9 which additionally contains from about 0.01% to about 1.25% by weight of the composition of a chelator in excess of the amount of chelator which will react with the bisbiguanide compound, said chelator being selected from the group consisting of nitrilotriacetic acid, ethylenediamine diacetic acid, kojic acid, maltol, ethyl maltol, calcium dihydrogen ethylenediamine tetraacetate, di-N-substituted ethylene diamine diacetic acids wherein the substituents are selected from the group consisting of ethyl and 2-hydroxyethyl and the pharmaceutically acceptable water-soluble salts of said chelators.